United States Patent [19]

Rao

[11] Patent Number: 5,260,188
[45] Date of Patent: Nov. 9, 1993

[54] METHOD OF TESTING A DONOR LIVER FOR TRANSPLANT

[75] Inventor: Prakash N. Rao, Pittsburgh, Pa.

[73] Assignee: University of Pittsburgh of the Commonwealth System of Higher Education, Pittsburgh, Pa.

[21] Appl. No.: 885,184

[22] Filed: May 19, 1992

[51] Int. Cl.⁵ ............................................. C12Q 1/00
[52] U.S. Cl. ..................................... 435/4; 435/7.21; 435/29; 436/29
[58] Field of Search ..................... 435/7.21, 1, 4, 7.1, 435/194, 29; 436/63

[56] References Cited

PUBLICATIONS

Adams, D. H. et al *Transplantation* vol. 47, pp. 479–482 (1989).
Polard et al. *Transplantation Proceedings*, vol. 22 pp. 2301–2302 (1990).
Hällgren et al *J Exp Med.* vol. 171 pp. 2063–2076 (1990).
Wells et al. *Transplantation*, vol. 50, pp. 240–243 (1990).
Hallgren et al *J Clin Investigation* vol. 85, pp. 668–673 (1990).
S. Todo et al., "Extended Preservation of Human Liver Grafts with UW Solutuion," *JAMA*, vol. 261, No. 5, (Feb. 3, 1989), pp. 711–714.
Shaw, B. W., Jr. et al., "Improved Results with Retransplantation of the Liver," *Transplantation Proceedings*, vol. 21, No. 1, (Feb. 1989), pp. 2407–2408.
A. W. Paulsen et al., *Transplantation Proceedings*, vol. 21, No. 1, (Feb. 1989), pp. 2337–2338.
H. Furukawa et al., "Effect of Cold Ischemia Time on the Early Outcome of Human Hepatic Allografts Preserved with UW Solution," *Transplantation*, vol. 51, No. 5, (May 1991), pp. 1000–1004.
T. E. Starzl et al., "Liver Transplantation," *The England Journal of Medicine*, vol. 321, No. 15, (Oct. 12, 1989), pp. 1014–1021.
G. Otto et al., "Preservation Damage in Liver Transplantation," *Transplantation*, vol. 42, No. 2, (Aug. 1986), pp. 122–124.
C. M. B. McKeown et al., "Sinusoidal Lining Cell Damage: The Critical Injury in Cold Preservation of Liver Allografts in the Rat," *Transplantation*, vol. 46, No. 2, (Aug. 1988), pp. 178–191.
P. N. Rao et al., "Purine Nucleoside Phosphorylase: A New Market for Free Oxygen Radical Injury to the Endothelial Cell", *Hepatology*, vol. 11, No. 2, (1990), pp. 193–198.
H. J. Mischinger et al., "Levels of Purine Nucleoside Phosphorylase (PNP) as a Viability Marker of Non-parenchymal Cells in Cold Preserved Livers," *Transplantation*, vol. 23, No. 1, (Feb. 1991), pp. 222–225.
S. Kakizoe et al., "Evaluation of Protocol before Transplantation and after Reperfusion Biopsies from Human Orthotopic Lever Allografts: Considerations of Preservation and Early Immunological Injury," *Hepatology*, vol. 11, No. 6, (Jun. 1990), pp. 932–941.
E. R. DeLong et al., "Comparing the Areas Under Two or More Correlated Receiver Operating Characteristic Curves: A Nonparametric Approach," *Biometrics*, vol. 44, No. 837–845, (Sep. 1988), pp. 837–845.
L. Makowka, R. D. et al., "Analysis of Donor Criteria for the Prediction of Outcome in Clinical Liver Transplantation," *Transplantation Proceedings*, vol. XIX, No. 1, (Feb. 1987), pp. 2378–2382.

*Primary Examiner*—Sam Rosen
*Attorney, Agent, or Firm*—Arnold B. Silverman; Suzanne Kikel

[57] ABSTRACT

A method for determining the suitability of an organ for transplant by performing one or more tests on the endothelial cells lining the blood vessels in the organ prior to the transplant operation. Specifically hyaluronic acid is used as the measure to determine liver transplant effectiveness.

8 Claims, 3 Drawing Sheets

METHOD OF TESTING A DONOR LIVER FOR TRANSPLANT

BACKGROUND OF THE INVENTION

1. Field of the Invention

The invention relates to a method of noninvasively testing a donor organ in preparation for transplant. More specifically, the invention is directed to a method for preoperatively testing for the suitability of an organ, such as a liver, and predicting postoperative transplant graft function.

2. Description of the Prior Art

In recent years, the medical field has developed techniques for saving and prolonging life by transplanting an organ, such as a liver into a patient.

The process of harvesting an organ from a donor, preserving the organ in transport, which involves keeping the organ cold, and subsequently transplanting the organ is associated with what is known as "preservation/reperfusion injury" In particular, in the preservation stage of handling an organ, such as a liver, the "injury" is localized in a specific region, mainly, in the cells which line the blood vessels. These cells are known as microvascular endothelial cells. This "injury" is the principal cause of nonfunction of the organ when transplanted into the patient.

In addition to transplanting a liver, other organs include a lung, a heart, and a small intestine. Both experimental and clinical evidence are available for the transplanting of a liver. For the remaining three organs, experimental evidence is available.

In liver transplants, up to 10% of human livers will not function following transplantation. This is referred to as primary nonfunction. If primary nonfunction occurs, the only alternative there is to save the patient's life is to retransplant another liver, which retransplantation operation has a subsequent 50% to 60% mortality rate.

Presently, there are no known tests available to the medical profession which can accurately and· in an noninvasive manner predict the severity of "preservation/reperfusion injury" prior to an operation which results in primary nonfunction of the graft, and the degree to which primary nonfunction will occur in the patient.

With regard to the health care system, the need for retransplanting an organ, particularly a liver, due to primary nonfunction increases the cost from a quarter of a million dollars up to approximately two million dollars. This increase in costs is due to two factors; the surgery of the retransplantation itself, and the intensive care unit.

There remains, therefore, a very real and substantial need to predict the extent of injury done to the microvascular endothelial cells during the preservation stage of the organ, and equating this extent of injury with the likelihood and degree of primary nonfunction occurring in the graft of a liver transplant patient.

There remains a further need to devise a method in which the likelihood of initial transplant failure of an organ is substantially decreased or eliminated For a test to be clinically useful, it should be noninvasive, rapidly performed, and reliable There remains a further need to devise a method for predicting graft organ function postoperatively by performing tests with these characteristics prior to the organ transplant operation.

SUMMARY OF THE INVENTION

The present invention provides a method for accurately and easily predicting prior to a liver transplant operation whether primary nonfunction in a patient will, in fact, occur, and the extent to which this condition will affect the graft function after the operation.

The invention involves the step of measuring specific parameters of the endothelial cells. Upon "preservation injury" the cells rupture, thereby releasing their contents into the fluid in which they are stored. These parameters or contents are purine nucleoside phosphorylase (PNP) and hyaluronic acid (HA). The method of the invention comprises the steps of predicting the degree of function and condition of a liver prior to its being transplanted by performing tests for levels of HA and/or PNP. These tests for HA and/or PNP levels are done before the organ transplant.

It is, therefore, an object of the invention to provide a method for noninvasively selecting for transplant an organ for a patient which resists organ failure due to primary nonfunction, and, therefore, which eliminates the need for a retransplant operation.

It is a further object of the invention to provide a method for transplanting an organ in a patient which effectively tests and measures the suitability of the organ in a transplant patient.

It is a further object of the invention to improve a method for transplanting a liver in a patient which effectively tests and measures the suitability of a liver in a transplant patient by performing tests prior to the transplant operation, and employing tests which are noninvasive, reliable, and quickly performed.

It is a further object of the invention to provide a method for transplanting an organ which comprises the steps of performing an HA and/or a PNP test on the organ prior to the transplant operation.

It is a further object of the invention to predict the extent of preservation injury of an organ and, therefore, the quality of a graft upon organ transplantation.

It is a broad object of the invention to predict postoperative organ function prior to the transplant operation.

It is still a further object of the invention to provide a method for transplanting an organ which keeps the costs of the operation down to a minimum.

It is a still further object of the invention to measure and consider the extent of rupture of the endothelial cells, and the level of their contents released into the fluid in which the cells are stored.

These and other objects of the invention will be more fully appreciated and understood from the following description of the invention.

DESCRIPTION OF THE PREFERRED EMBODIMENTS

As used herein, the term "patient" includes any member of the animal kingdom including but not limited to human beings.

The terms aspartate transaminase (AST) and alanine transaminase (ALT) are known to be enzymes which leak from the liver cells. Their levels in international units/liter (IU/l) are elevated following injury to the parenchymal cells of the liver.

It has been determined that a key factor for measuring the suitability of an organ, particularly a liver, for transplant is to use the specific parameters of the endothelial cells which line the blood vessels as indicators of preservation injury.

As "preservation injury" is localized to the endothelial cells, these cells tend to rupture, thereby resulting in the contents of the cell flowing into the fluid of the blood vessels. The present invention involves measuring the levels of at least one of two parameters of the cells, namely, purine nucleoside phosphorylase (PNP) and hyaluronic acid (HA). Measurements for determining the levels of these two endothelial cell components are done on the washout effluent of the donor organ before it is transplanted. The methods for obtaining the quantities or levels of HA and PNP in organs are well-known to those skilled in the art. While measurements of the levels of HA had previously been known, they were used solely after the operation as a measure of liver function, and as an indicator of acute rejection in the postoperative period.

Embodiments of the invention employ an HA and/or a PNP test to measure HA and/or PNP quantities or levels in the washout effluent of the donor organ, such as a liver, before the liver is transplanted These tests are noninvasive, reliable, and can be performed in less than three hours, with the PNP test being completed in about 45 minutes.

One such testing for HA levels may be by employing a test known as the "PHARMACIA HA TEST", which is manufactured by Pharmacia Diagnostics AB, S-75182, Uppsala, Sweden, or any test which is similar. These tests are radiometric assays for determination of hyaluronic acid in serum and the fluids which store the contents released from the ruptured endothelial cells following "preservation injury" to the liver. A clear rise of the HA level is associated with liver disease and in rejection of the liver. See generally: 1) Otto G., Wolff H., Uerlings I., and Gellert K., "Preservation damage in liver transplantation: Influence of rapid cooling,", *Transplantation*, 1986, Vol. 42, pp. 122-124; 2) McKeown, C. M. B., Edward V., Phillips M. J., Harvey P. R. C., Petrunka C. N., and Strasberg S. M., "Sinusoidal lining cell damage: The critical injury in cold preservation of liver allografts in the rate,," *Transplantation* 1988, Vol. 46, pp. 178-191; 3) Rao P. N., Walsh T. R., Makowka L., et al., "Purine nucleoside phosphorylase: A new marker for free oxygen radical injury to the endothelial cell," *Hepatology*, 1990, Vol. 11, pp. 193-198; and 4) Mischinger H. J., Rao P. N., Todo S. et al., "Levels of purine nucleoside phosphorylase (PNP) as a viability marker of nonparenchymal cells in cold preserved livers," *Transplant Proc.*, 1991, Vol. 23, pp. 222-225.

Hyaluronic acid is an unbranched high-molecular weight polysaccharide. It consists of repeating disaccharide units of glucuronate-$\beta$1,3-N-acetyl-glucosamine linked together by $\beta$1,4-bonds.

The PHARMACIA HA TEST is based on the use of specific hyaluronic acid binding proteins, HABP, isolated from bovine cartilage. The hyaluronic acid in an effluent sample from the organ to be transplanted reacts with $^{125}$I-labelled HABP in solution. The unbound $^{125}$I-HABP is then quantitated by incubating with HA covalently coupled to Sepharose® particles of small size and low density. Separation is performed by centrifugation followed by decanting. The radioactivity bound to the particles is measured in a gamma counter and the response is inversely proportional to the concentration of HA in the sample.

In general, the present invention is performed by doing the following:

The washout effluent from the donor liver is centrifuged at 4° C. to remove red blood cells, and the samples are analyzed for HA levels at room temperature, a radiometric assay such as the HA kit marketed by PHARMACIA, discussed hereinbefore. This kit contains all the reagents, and meets the standards required for the assay. The assay is performed according to the instructions of the manufacturer of the kit.

As the principal cause of primary nonfunction in clinical liver transplantation is "preservation injury" to the endothelial cells of the microvasculature, the levels of HA and PNP in the effluent could predict early graft function in clinical liver transplantation.

In order to provide further disclosure of the invention, the following examples will be given:

EXAMPLE 1

Material and Method

Several perfused rat livers were used in an experimental study to determine the effect of cold preservation or ischemia and warm reperfusion on effluent levels of HA and PNP, and to determine whether these levels could be used to predict graft function. The livers were harvested from male Lewis strain rats and static preserved in cold 4° University of Wisconsin solution for either 16, 24, 26, 48, or 50 hours, hereinafter referred to as Group 1. At the end of the preservation period, the livers were flushed with 10 cc of cold lactated ringer's solution.

The rat livers which had been preserved for 16, 24, or 48 hours were subsequently reperfused at 37° C. for 2 hours with an asanguinous Krebs Henseleit buffer containing 2% bovine serum albumin. This group of livers is hereinafter referred to as Group 2. These three preservation time periods for Group 2 were selected since past experience had shown that livers which had been preserved for 16, 24, or 48 hours had undergone a certain degree of preservation injury, and were associated with survival rates of 85%, 50%, and 20%, respectively, after 3 weeks.

Additionally, control perfusions with freshly harvested, nonpreserved livers were carried out for 2 hours, hereinafter referred to as Group 3.

Figure 1:
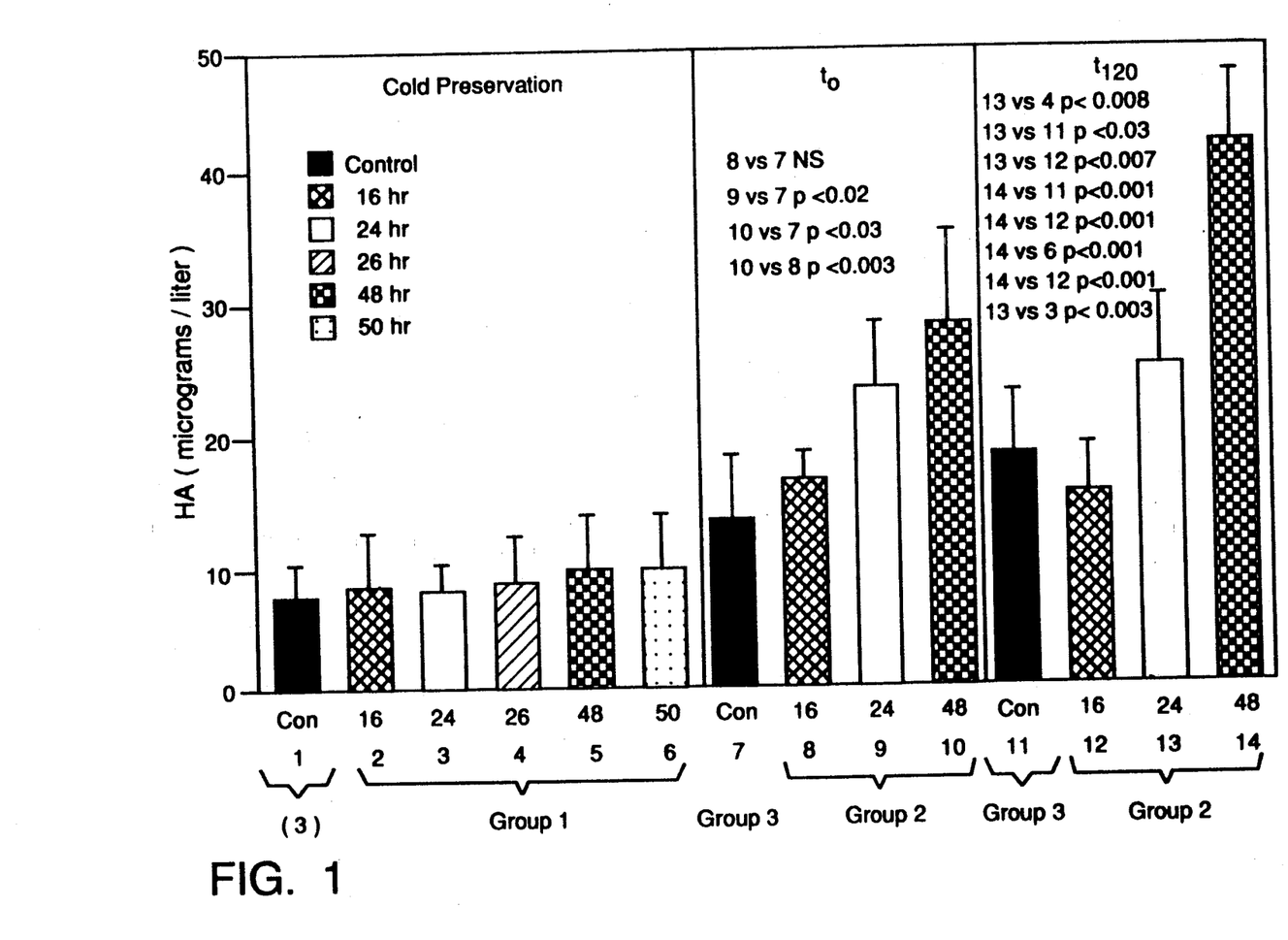
FIG. 1 is a graph of the results for the mean HA levels for the several groups of Example 1 which depicts the effluent levels after cold preservation, early reperfusion ($t_0$), and the end of reperfusion ($t_{120}$), where the vertical axis shows the HA levels in micrograms/liter and the horizontal axis indicates the several groups.

Samples of the flush from preserved livers and the effluent of Group 2 were collected periodically during the reperfusion period, and were assayed for HA, PNP, and transaminases (AST and ALT) levels. The preservation and reperfusion procedures were performed under sterile conditions. The effluent samples for Group 2 were collected at the beginning of reperfusion ($t_0$), 1 hour after reperfusion ($t_{60}$), and at the end of reperfusion ($t_{120}$), which was 2 hours later. FIG. 1 shows the results for only $t_0$ and $t_{120}$ which are values at the beginning and end of reperfusion, respectively.

Assay Techniques

The PNP levels were assayed by the breakdown of inosine to uric acid, as measured by the increase of absorbance at 293 nm in a coupled assay system with xanthine oxidase. PNP from calf's spleen (>99% pure) and xanthine oxidase from cow's milk was purchased from Boehringer Mannheim located in Indianapolis, Ind. The inosine was purchased from Sigma Chemical Company, St. Louis, Mo. The PNP concentration in the effluent samples was read from a standard curve prepared for pure PNP.

For the HA measurements, radiometric assays were used with kits marketed by Pharmacia Diagnostics (Uppsala, Sweden), which was discussed hereinbefore. All samples, including standards, were run in duplicate. The variation in the results for the samples ranged from about 1.5% to about 2.2%.

With regard to the AST and ALT levels in the samples, the release of these hepatocellular enzymes into the perfusate was determined on a Technicon RA-500 analyzer using commercially available kits.

Statistical Analysis

Statistical differences between the experimental groups were studied by a one-way analysis of variance. A one-way analysis of variance refers to a procedure to deter mine if differences or variations between two experimental groups are due to random change alone or whether the differences are genuine. One way refers to the fact that one parameter such as HA, PNP, AST, ALT, etc., is studied at a time. A "p" value of $p<0.05$ was established as the standard for significant differences in levels of either PNP, HA, AST, or ALT between groups. This small case "p" stands for probability. The notation "$p<0.05$" means that the probability that the differences between groups is due to random chance is less than 5 in 100. A linear regression analysis was used to confirm the effect of cold ischemia on the effluent levels of HA and PNP, and to determine whether these levels could be used to predict post reperfusion hepatocellular function. "$R^2$" stands for a linear regression coefficient. An equation "$R^2=38\%$" means that 38% of the samples are explained or accounted for by the parameter, e.g. HA level in the data.

Results

HA Levels

The results for the mean HA levels of Groups 1, 2, and 3 are shown in the graph of FIG. 1. As stated herein before, Group 1 consists of the rat livers which underwent 16, 24, 26, 48 and 50 hours of cold preservation only without reperfusion. Group 2 consists of the rat livers which had undergone 16, 24, and 48 hours of cold preservation followed by warm reperfusion. Group 3 consists of rat livers which are the control group. These are the freshly-harvested, nonpreserved but reperfused livers.

In FIG. 1, Group 3 is indicated as "Con". Groups 1 and 3 are represented to the left of FIG. 1 under "Cold Preservation." Group 1 is indicated symbolically by numbers 16, 24, 26, 48, and 50 underneath the bars which represent the levels of HA. Groups 2 and 3 are represented in the last two sections to the right of FIG. 1, where $t_0$ represents the beginning time period for reperfusion, and $t_{120}$ represents the end of time period for reperfusion after two hours The numbers 16, 24, and 48 appear under the bars representing the HA levels. Numbers 1 through 14 appear under the members of each group in the three sections of FIG. 1, and help in explaining and giving a better understanding for comparisons which were made for the HA levels between the members of the three groups. This will become more apparent when giving the following experimental results for the HA levels of the livers which had undergone cold preservation, those which had undergone cold preservation followed by reperfusion, and the control group. For instance, a comparison in the HA levels between the 24 hour liver of Group 2 indicated by number 9 in FIG. 1 and the control liver of Group 3 which is number 7 in FIG. 1 is $p<0.02$. As stated hereinbefore, any value for p less than 0.05 is considered to be highly significant.

The mean HA levels at the end of 16, 24, 26, 48, and 50 hours of cold preservation for Group 1 were $9.0\pm2.7$; $8.85\pm1.6$; $9.2\pm2.0$; $10.12\pm3.0$; and $10.2\pm3.1$ micrograms/liter, respectively. These levels were approximately the same for Group 3, the control nonpreserved livers, which were $8.0\pm2.2$ micrograms/liter. These HA levels are represented by the bars to the left of FIG. 1 under "cold preservation." In effect, there were no significant differences in HA levels for these two groups, that is, Groups 1 and 3.

For Group 2, which underwent 16, 24, and 48 hours of cold preservation followed by reperfusion, the effluent levels at the beginning of reperfusion were $17.5\pm1.22$; $3.14\pm5.24$; and $28.27\pm6.82$ micrograms/liter, respectively. These levels are shown by the bars in the second section of FIG. 1 under $t_0$ The effluent levels at $t_0$ for the control perfusion livers of Group 3 were $14.0\pm4.44$ micrograms/liter. As can be seen in FIG. 1, at $t_0$, the HA level for "Con" and "16" are almost the same. This is represented by "8 vs 7 NS" in FIG. 1. However, the HA levels for "24" (Number 9) and "48" (number 10) at $t_0$ are significantly higher than that for "Con" (number 7) at $t_0$ These comparisons are shown as being $p<0.02$ for number 9 vs number 7, and $p<0.03$ for number 10 vs. number 7 in FIG. 1. When comparing "10" to "8", the "p" value is less than than 0.003.

Generally, the increase in the release of HA from the livers for Groups 2 and 3 continued as reperfusion progressed. The HA levels at $t_{120}$, the end of reperfusion, for "24" and "48" in the last section of FIG. 1 were significantly higher than that for "Con". The comparisons of of the HA levels for "24" and "48" to "Con" are represented by "13 vs 11 $p<0.03$" and "14 vs. 11 $p<0.001$", respectively. Also, the HA levels for "24" and "48" of Group 2 were significantly higher than "16" of Group 2. These comparisons are shown as "13 vs 12 p.$<0.007$" and "14 vs 12 $p<0.001$", respectively.

The HA levels at $t_{120}$ for "24" and "48" of Group 2 as compared to "26" and "50" of Group 1 were also significantly higher. These comparisons were generally $p < 0.001$. The "48" hour of Group 2 at $t_{120}$ is compared to "50" of Group 1 and is indicated as "14 vs 6 p. <0.001" in the $t_{120}$ section in FIG. 1.

PNP Levels

Figure 2:
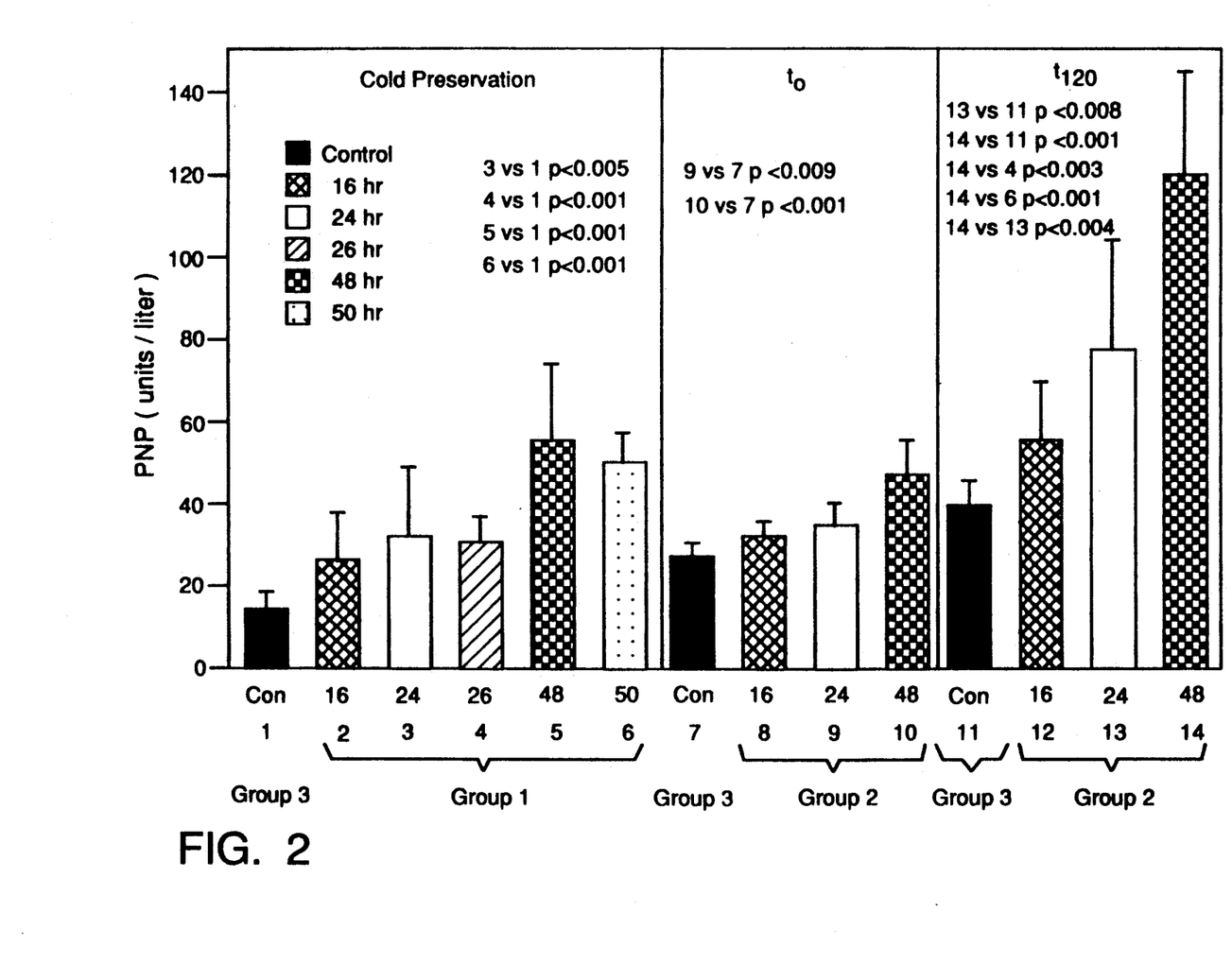
FIG. 2 is a graph of the results for the mean PNP levels for the several groups of Example 1, which depicts the effluent levels after cold preservation, early reperfusion ($t_0$), and the end of reperfusion ($t_{120}$), where the vertical axis shows the PNP levels in units/liter and the horizontal axis indicates the several groups.

Similar comparisons for effluent PNP levels for Groups 1-3 were made and appear in FIG. 2 where the same symbols and/or representations appear as they do in FIG. 1.

The mean PNP levels for "16", "24", "26", "48", and "50" hours for Group 1, were $26.25 \pm 11,43$; $32.88 \pm 16,46$; $31.16 \pm 5.46$; $55.88 \pm 18.87$; and $50.98 \pm 17.86$ units/liter, respectively. As can be seen, the PNP values for "24" to "50" for the cold preservation Group 1 were significantly higher than the effluent PNP levels for the control, nonpreserved livers "Con" of Group 3. This is represented in FIG. 2 by the following: "3 vs 1 $p < 0.005$"; "4 vs 1 $p < 0.001$"; 5 vs 1 $p < 0.001$"; and "6 vs 1 $p < 0.001$". At the end of reperfusion, $t_{120}$, the PNP levels for "16", "24", and "48" of Group 2 were $56.25 \pm 14.65$, $72.0 \pm 28.67$, and $120.0 \pm 5.77$ units/liter, respectively.

In referring to the far right hand section $t_{120}$ of FIG. 2, it can be seen that the PNP levels at the end of reperfusion $t_{120}$ following 16 hours of cold preservation which is identified by number 12, were approximately the same as the control perfusions "Con" identified by number 11. The PNP levels for these livers were around $37.67 \pm 5.92$ units/liter. However, the PNP levels at the end of reperfusion $_{120}$ following 24 or 48 hours, identified by numbers 13 and 14 in FIG. 2, were significantly higher than the control livers (number 11) as indicated by 13 vs 11 $p < 0.008$ and 14 vs 11 $< 0.001$, respectively, under the $t_{120}$ section in FIG. 2, and significantly higher than the livers at the end of 26 hours (number 4) and 50 hours (number 6) of the preserved livers of Group 1, $p < 0.003$ and $p < 0.001$), respectively in FIG. 2.

AST Levels

The AST levels at the end of reperfusion $t_{120}$ following 16 and 24 hours of cold preservation were $128.0 \pm 28.62$ and $145.29 \pm 33.44$ international units/liter (IU/l), respectively. These levels were approximately the same as to those observed at the end of reperfusion in the control non-preserved livers (Con), which were $112.0 \pm 36.96$ IU/L.

However, the AST levels for the livers at the end of reperfusion following 48 hours of cold preservation were $641.17 \pm 327.29$ IU/l which is significantly higher than those livers observed in the control group ($p < 0.004$), and those $p < 0.004$ observed at the end of 50 hours of cold preservation ($p < 0.03$).

ALT Levels

The profiles for the ALT levels were similar to those observed for the AST levels. Although reperfusion following either 16 or 24 hours of cold preservation did not apparently cause hepatocellular damage, significantly higher levels of ALT were observed at the end of reperfusion following 48 hours of cold preservation ($p < 0.02$).

Linear Regression Analysis

Regression analysis demonstrated that the elevation of HA and PNP levels during reperfusion were dependent on the period of cold preservation. See Table 1 below.

TABLE 1

PREDICTIVE VALUES OF COLD ISCHEMIA
TIME FOR HA AND PNP VALUES
ON REPERFUSION ($t_0$) and ($t_{120}$)*

|  | 1 $R^2$ (%) |  | 2 $R^2$ (%) |  | 3 $R^2$ (%) |  | 4 $R^2$ (%) |  |
| --- | --- | --- | --- | --- | --- | --- | --- | --- |
| Parameter | HA ($t_0$)** | 'p' | HA ($t_{120}$)*** | 'p' | PNP ($t_0$) | 'p' | PNP ($t_{120}$) | 'p' |
| CIT* | 49.30 | <0.002 | 71.60 | <0.001 | 67.20 | <0.001 | 68.70 | <0.001 |

*CIT = Cold Ischemia Time
**$t_0$ = Beginning of Reperfusion
***$t_{120}$ = End of Reperfusion Table 1 presents the predictive values for HA and PNP levels for those livers treated under cold preservation followed by warm reperfusion, which are those of Group 2. The linear regression, $R^2$, for the HA levels at $t_0$ is 49.30%, which means that 49.30% of the change in HA levels may be accounted for as explained by the period of cold preservation. This is significant at a probability level of $p < 0.002$. This data is shown in column 1 in Table 1. At the end of reperfusion $t_{120}$, the linear regression analysis, $R^2$, shows 71.60% of the samples as being accounted for with regard to the HA levels with a probability factor $p < 0.001$. See column 2 of Table 1.

For the PNP predictive values, at $t_0$, $R^2$ is 67.20%, and "p" is $< 0.001$. At $t_{120}$, $R^2$ is 68.70%, and "p" is $< 0.001$.

TABLE 2

PREDICTIVE VALUE OF HA AND PNP ($t_0$)*
for AST AND ALT $t_{(120)}$**

|  | 1 $R^2$ (%) | 2 | 3 $R^2$ (%) | 4 |
| --- | --- | --- | --- | --- |
| Parameter | AST ($t_{120}$) | 'p' | ALT ($t_{120}$) | 'p' |
| HA ($t_0$) | 34.57 | <0.009 | 26.73 | <0.03 |
| PNP ($t_0$) | 62.10 | <0.001 | 59.80 | <0.001 |

*$t_0 \rightarrow$ Beginning of Reperfusion
**$t_{120} \rightarrow$ End of Reperfusion Table 2 represents the predictive value of HA and PNP levels at the beginning of reperfusion ($t_0$) for AST and ALT levels at the end of reperfusion ($t_{120}$). As stated hereinbefore, these predictive values are highly significant. As shown in Table 2, the $R^2$ for the AST level at $t_{120}$ (column 1) is 34.57% as predicted by the HA level at $t_0$ This means that the 34.57% of the change in AST at $t_{120}$ which is the end of reperfusion may be explained by the variation in HA at $t_0$ which is the beginning of reperfusion. This is highly significant at $p < 0.009$ (column 2, Table 2).

The $R^2$ for the ALT level at $t_{120}$ is 26.73% as predicted by the HA level at $t_0$ (column 3). This is significant with $p < 0.03$. The linear regression $R^2$ for AST at $t_{120}$ based on the PNP levels as to the predictive parameter is 62.10% (column 1). This is significant at p<0.001 (column 2). The $R^2$ for ALT levels at $t_{120}$ as predicted by PNP levels at $t_0$ is 59.80% (column 3) with a significance of p<0.001 (column 4). Table 2 therefore indicates, based on linear regression analysis, that HA and PNP levels at the beginning of reperfusion can predict hepatocellular function, as measured by AST and ALT, at the end of reperfusion with a significant degree of accuracy.

Figure 3:
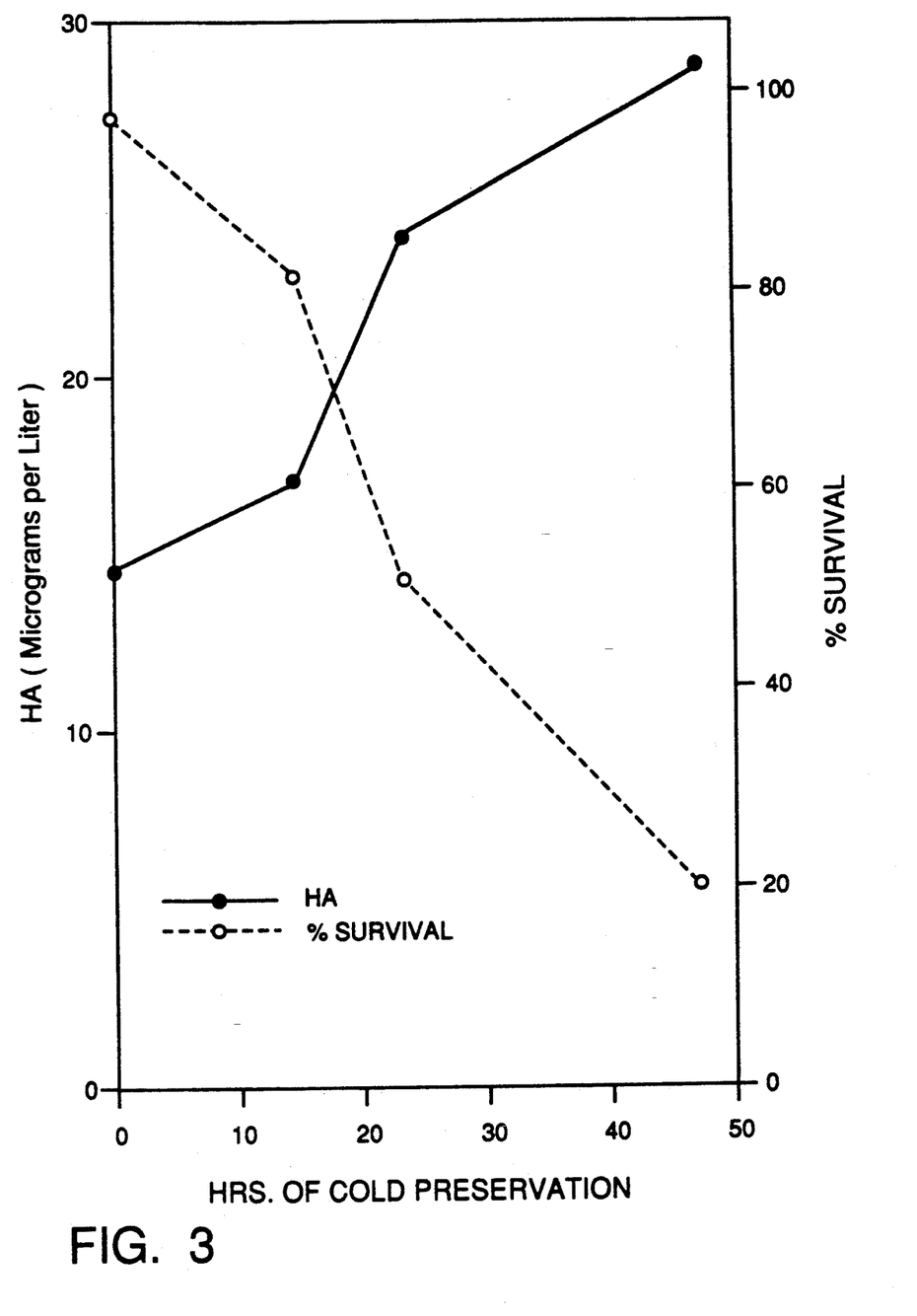
FIG. 3 is a graph showing a correlation between the graft outcome and the effluent HA levels at the beginning of reperfusion for Example 1, where the right vertical axis indicates the survival percentage, the left vertical axis indicates HA levels in micrograms per liter; and the horizontal axis indicates the hours of cold preservation.

FIG. 3 is a graph showing a correlation between the results of the graft and the effluent HA levels at the beginning of the reperfusion period $t_0$. The hours of cold preservation appear on the bottom axis, and the survival rate and the levels of HA appear on the two parallel, vertical axes.

As can be seen, there is an increase in effluent HA levels at the start of reperfusion following increasing periods of cold preservation, in particular, for 16, 24, and 48 hours. There is a corresponding decrease in graft survival for these same time periods at the end of 3 weeks with almost a 100% survival rate at zero hours of cold preservation, around 70% survival rate, for 20 hours of cold preservation, and only 20% survival rate at 50 hours of cold preservation.

Reperfusion following cold preservation for the several livers of Group 2 resulted in significant elevations of HA levels in the effluent as a consequence of endothelial cell injury. This is consistent with our earlier data by Rao, P. N., Walsh, T. R., Makowka, L., Liu T., et al. "Inhibition of Free Radical Generation and Improved Survival by Protection of the Hepatic Microvascular Endothelium by Targeted Erythrocytes in Orthotopic Rat Liver Transplantation", *Transplantation*, 1990, Vol. 49, p. 1055, and the findings of Caldwell-Kenkel, Jr., Thurman, R. G., LeMasters, J. J., "Liver Preservation for Transplantation: Early Loss of Nonparenchymal Cell Viability", *Transplantation*, 1988, Vol. 45, p. 834, and the findings of Thurman, R. G., Marzi, I., Seitz, G., Thies, J., Lemasters, J. J., Zimmerman, F., "Hepatic Reperfusion Injury Following Orthotopic Liver Transplantation in the Rat", *Transplantation*, 1988; Vol. 46, p. 502, who also demonstrated increasing injury to the microvascular endothelial cell on reperfusion following cold ischemia.

The injury was not manifested with cold preservation alone, but the severity of reperfusion injury was dependent on the period of cold preservation (Table 1).

Unlike the HA levels, the PNP levels were significantly elevated in the washout effluent of livers which had undergone cold preservation only. (Group 1) This was followed by a further significant increase of the PNP levels during warm reperfusion.

Effluent levels of HA and PNP were elevated rapidly following reperfusion. A linear regression analysis of the data indicated that these levels could be used to predict post reperfusion hepatocellular function with a significant degree of accuracy. See Table 2. Preliminary data from syngenic transplant experiments using livers that were preserved for 24 hours prior to transplantation showed a significant increase in effluent HA levels in livers that failed within three weeks, as compared to those that survived. (Of these livers, 50% survived after three weeks.) That is, the HA levels for the livers that failed were 30.44±2.79 micrograms/liter (p<0.018), as compared to those which survived where the HA levels were 9.86±3.85 micrograms/liter.

A large number of parameters have been used in the past to predict post transplant graft viability. Most of these methods are invasive, time consuming, nonspecific, and thus, of limited clinical value. The present study in this Example 1 demonstrates that effluent levels of HA and PNP can be used as noninvasive, early markers of preservation injury to the microvascular endothelial cell, and could prove to be accurate diagnostic indices of graft viability following liver transplantation.

EXAMPLE 2

The experimental data of Example 1 showed that effluent levels of HA and PNP could predict the degree of preservation injury to the microvascular endothelial cell, and therefore, graft function and its outcome.

A clinical study of orthotopic liver transplantation was made to confirm these findings.

Materials and Method

Thirty-two (32) human livers were transplanted orthotopically to randomly selected human adult primary recipients with negative lymphocytotoxic crossmatches. Of these thirty-two, 29 were treated with FK506 and a low dose of steroids (20 mg/day); and 3 were treated with cyclosporine and the conventional high dose of steroids, starting with 200 mg/day of methylprednisolone. During and after procurement of the steroids, the livers were infused with University of Wisconsin solution at 4° C. After varying periods of static cold storage, which was 13.3±3.2 hours, the livers were unpackaged and reinfused with lactated ringer's solution at 4° C. For each of the 32 transplant operations, the first 50 ml of the reperfusion effluent was collected from the infrahepatic vena cava. Twenty-three (23) of the samples were collected at the operating table after the upper caval anastomosis was completed, whereas the other 9 livers were reperfused on the back table before implantation was started. These 9 livers were reflushed with 300 ml of cold University of Wisconsin solution before further storage. All thirty-two, 50 ml effluent collections were centrifuged at 2000 rpm for 10 minutes to remove the erythrocytes, and the aliquots were analyzed for HA (100 microliters) and PNP (20 microliters) levels. The 32 livers used in this experiment satisfied the established preoperative criteria. See: Kakizoe S., Yanaga K., Starzl, T. E., Demetris, A. J., "Evaluation of protocol before transplantation and after reperfusion biopsies from human orthotopic liver allografts; Considerations of preservation and early immunological injury", *Hepatology*, 1990, Vol. 11, pp. 932-941.

There were an additional 3 livers which did not satisfy these criteria, in that they had at least greater than 60% macro and microvascular steatosis and, therefore, were not used in this particular study. It is interesting to note, however, that these three livers had effluent HA levels of 580, 596, and 534 micrograms/liter, respectively.

Assays

The PNP levels were assayed by the breakdown with xanthine oxidase of inosine to uric acid, as measured by the increase in absorbance at 293 nm in a coupled assay system. See Rao et al. and Mischinger et al. cited hereinbefore. For the HA measurements, radiometric assays were used with kits marketed by Pharmacia Diagnostics (Uppsala, Sweden), which was discussed hereinbefore. All samples, including standards, were run in duplicate.

Graft function after transplantation was stratified by the criteria of Kakizoe, et al. cited hereinbefore and also see: Makowka, L., Gordon, R. D., Todo, S. et al., "Analysis of donor criteria for the prediction of outcome in clinical liver transplantation," *Transplant Proc.,* 1987, Vol. 19, pp. 2378-2382. Peak serum AST levels of less than about 500 IU/l and peak serum ALT levels less than about 1000 IU/l at any time during the first postoperative week were indications of "good grafts". Levels of AST and ALT higher than 500 IU/l and 1000 IU/l, respectively, were considered as "poor grafts".

RESULTS

Linear Regression

A linear regression analysis was used to study whether effluent levels of HA and PNP correlated with and were therefore predictive of early graft function as defined by the AST and ALT levels (serum transaminase). It was observed that a very high degree of correlation existed between effluent HA levels as a marker of preservation injury and postoperative AST and ALT levels indicating the way the graft would function following transplantation. That is, for AST the linear regression factor, $R^2$ was equal to 37.30%, and the probability value was $p<0.001$, and for ALT, $R^2$ was equal to 43.20% and $p<0.001$. The notation "$p<0.001$" means that there probably is less than one in a thousand that the observed predictive value of HA for AST or ALT is due to random chance The equation "$R^2=40\%$" means that the 40% of the variation in AST and ALT levels may be explained by variations in HA levels.

A lesser degree of correlation was observed between effluent PNP levels as an indication of preservation injury and postoperative AST and ALT levels indicating the manner in which the graft functioned following transplantation. That is, for the AST level, $R^2=19.10\%$ and $p<0.02$, and for the ALT level, $R^2 11.50\%$, and $p<0.07$.

The above statistical data are shown on Table 3 below:

TABLE 3

| PREDICTIVE VALUE OF EFFLUENT HA AND PNP LEVELS FOR POST TRANSPLANT LIVER FUNCTION | | | | |
|---|---|---|---|---|
| PARAMETER | $R^2$ FOR AST (%) | P | R FOR ALT (%) | P |
| HA | 37.30 | <0.001 | 43.20 | <0.001 |
| PNP | 19.10 | <0.02 | 11.50 | <0.07 |

Stratification of HA and PNP Levels

Using the criterion of Kakizoe et al. and Makowka et al., when the data was stratified in the 30 cases where the levels of AST and ALT were available, based on the postoperative AST levels, 19 grafts were classified as "good" and 11 as "poor". The mean effluent HA level for the 19 grafts in the "good" graft category was 256.0±132.0 micrograms/liter. This mean HA level was significantly lower than the mean HA level for the 11 "poor" grafts, which HA levels were 485±139.0 micrograms/liter. These data are shown in the second and third columns of Table 2. The probability factor is $p<0.0003$, as shown in the fourth column of Table 4, as shown below:

TABLE 4

| | EFFLUENT HA AND PNP LEVELS IN GOOD AND POOR LIVERS* | | | | | |
|---|---|---|---|---|---|---|
| 1 | 2 | 3 | 4 | 5 | 6 | 7 |
| PARAMETER | AST <1500 Iu/lt (n = 19) | AST 1500 Iu/lt (n = 11) | P | ALT <1000 Iu/lt (n = 17) | ALT >1000 Iu/lt (n = 13) | P |
| HA (micrograms/liter) | 256.0 ± 132.0 | 485.0 ± 139.0 | 0.0003 | 256.0 ± 140.0 | 485.0 ± 439.0 | 0.0017 |
| PNP (U/lt) | 91.3 ± 42.9 | 135.2 ± 50.0 | 0.026 | 88.4 ± 43.6 | 132.2 ± 47.6 | 0.016 |

*Good Grafts: AST levels <1500 Iu/lt and ALT levels <1000 Iu/lt at any time during 1st postoperative week.
Poor Livers: AST Levels >1500 Iu/lt and ALT levels >1000 Iu/lt at any time during 1st preoperative week.

When the data were stratified on the basis of postoperative ALT levels, 17 grafts were classified as "good" and 13 as "poor". Mean HA levels in the "good" grafts were 256.00±140.00. These figures were significantly lower than the mean HA levels in the "poor" grafts of 485.0±139.0 micrograms/liter. These figures are shown in columns 5 and 6 of Table 4. The probability factor is $p<0.0017$ as shown in column 7 of Table 4 for the HA level data.

Still referring to Table 4, mean effluent PNP levels in the "good" grafts classified on the basis of AST levels were 91.3±42.9 units/liter (column 2 of Table 4). The figures were significantly lower than the mean PNP levels in the "poor graft" group of 135.2±50 units/liter. (Column 3, Table 4) The probability factor is $p<0.026$. (Column 4 of Table 4) When postoperative graft function was stratified as "good" or "bad" on the basis of ALT levels, the mean PNP level in the "good" grafts was 88.4±43.6 units/liter which was significantly lower than the PNP levels in the "poor" graft category of 132.2±47.6 units/liter. The probability factor is $p<0.016$. (See columns 5, 6, and 7 of Table 4.)

The "good grafts" had AST levels<1500 IU/l and ALT levels<1000 IU/l at any time during first postoperative week. The "poor livers" had AST levels >1500 IU/l and ALT levels>1000 IU/L at any time during first postoperative week.

The results in this example as shown in Table 4 indicate that livers classified as "good" on the basis of postoperative AST levels had significantly lower effluent HA levels ($p=0.0003$) than livers which were classified as "poor." Similar profiles were observed when livers were classified as "good" or "poor" on the basis of ALT levels ($p=0.0017$).

PNP levels were less sensitive with "p" values of 0.026 and 0.016, respectively, when postoperative graft function was stratified as the basis of AST or ALT levels.

An hypothetical cutoff ceiling for HA used to discriminate between "good" and "bad" livers, which were those at risk of early graft failure, suggested a value between 400 and 430 micrograms/liter. A hypothetical cutoff ceiling for PNP suggested a value between 95.0 and 105.0 units/liter.

Five cases in this study failed from primary nonfunction. Since all 32 livers used in this study satisfied established preoperative criteria regarding their suitability as donor organs, none of these livers should have failed from primary nonfunction. Effluent HA levels in these 5 cases were 440, 480, 568, 600 and 585 micrograms/-liter, respectively. These HA levels were indicative of severe preservation injury to the microvasculature. In spite of satisfying preoperative criteria, all 5 livers subsequently demonstrated histological evidence of severe preservation injury.

From this study, the following was concluded: 1) There is a high degree of correlation between effluent HA levels and postoperative graft function, as reflected by the AST and ALT levels. 2) There is a high degree of correlation between HA levels and graft outcome. 3) An HA level of between 400 and 430 micrograms/liter could be used to distinguish between "good" livers and "bad" livers. That is, levels below these values are "good", and those above these levels are "bad", "bad" meaning at risk of early graft failure.

EXAMPLE 3

A prospective clinical study was conducted to confirm the findings of Example 2. In this study, 34 consecutive antibody crossmatch negative livers were transplanted in 34 recipients treated with FK506. Prior to this, all livers were preserved in University of Wisconsin solution at 4° C. Later, on the back table of the operating room, the donor livers were flushed through the portal vein upper vena cava was clamped, and the collected returning effluent was analyzed for HA levels by radioimmunoassay.

The livers were reperfused with University of Wisconsin solution, and were transplanted within 6 hours. Three (3) livers with levels of HA greater than 400 micrograms/liter failed from primary nonfunction, which necessitated retransplantation, on the other hand, all the livers with HA levels less than 400 micrograms per liter functioned optimally.

The experimenter concluded that HA values can be rapidly determined within 3 hours while the liver is being prepared for transplantation on the back table of the operating room. Analysis of the HA value can be used to discriminate in advance between those livers which are suitable for transplantation and those which are at "high" risk for developing primary nonfunction.

Both the HA and PNP tests are easy to perform and can be rapidly assayed within 3 hours.

It is, therefore, taught by the invention that an effluent HA level less than or equal to 400 micrograms/liter and an effluent PNP level less than or equal to 135 micro grams/liter can rapidly discriminate livers suitable for transplantation prior to the transplant operation. At the same time, a HA level of greater than 400 micrograms/liter and a PNP level greater than 135 micrograms/liter would appear to indicate the presence of moderate to severe preservation injury to the microvascular endothelial cells, and, therefore, a significant risk that the graft would fail due to primary nonfunction.

Of the two tests, the HA test is the preferred test, and the PNP test is the less preferred. However, the PNP test can be used to adequately indicate the extent of preservation injury. Also, both tests can be used on the same liver with proper adjustments to the procedure, the 400 and 135 $\mu$gm/l threshholds, and the interpretations of the results of the tests.

Whereas particular embodiments of this invention have been described above for purposes of illustration, it will be evident to those persons skilled in the art that numerous variations of the details of the present invention may be made without departing from the invention as defined in the appended claims.

For instance, even though liver transplants have been given as examples, the invention can be used for other transplant organs, such as the heart, the lung, and the small intestine or bowel.

I claim:

1. A method of testing a harvested and preserved liver to be transplanted, the steps comprising:
    prior to the transplanting of said liver while said liver is in said preserving stage, testing the washout effluent of said liver to determine the level of hyaluronic acid in said effluent, and
    employing the result of said testing to determine whether said transplanting of said liver will be successful or will be primary nonfunction.

2. The method of claim 1, the steps further comprising:
    selecting said liver as being suitable for said transplanting if said effluent level of said hyaluronic acid is at least less than or equal to 400 micrograms/liter.

3. The method of claim 2, the steps further comprising:
    employing the value of said level of said hyaluronic acid as an indicator that the extent of the preservation injury occurring to the microvascular endothelial cells of said liver is minimal and determining that this value will result in a high degree of success in said transplanting of said liver.

4. The method of claim 1, the steps further comprising:
    rejecting said liver for said transplanting if said effluent level of said hyaluronic acid is greater than 400 micrograms/liter.

5. The method of claim 3, the steps further comprising:
    employing the value of said level of said hyaluronic acid as an indicator that the extent of the preservation injury to the microvascular endothelial cells of said organ is moderate to severe, and determining that this value will result in a high degree of primary nonfunction in said transplanting of said liver.

6. The method of claim 1, wherein said testing is performed in at least three hours prior to said transplanting of said liver.

7. A method of claim 1, the steps further comprising:
    prior to the transplanting of said organ while said organ is in said preserving stage, testing the washout effluent of said organ to determine the level of purine nucleoside phosphorylase in said effluent.

8. The method of claim 1, the steps further comprising:
    centrifuging the washout effluent from said liver at about 4° C. to remove red blood cells,
    analyzing for HA levels at about 37° C., and
    using a radiometric assay for said analyzing of said HA levels.

* * * * *

UNITED STATES PATENT AND TRADEMARK OFFICE
CERTIFICATE OF CORRECTION

PATENT NO. : 5,260,188

DATED : November 9, 1993

INVENTOR(S) : Prakash N. Rao

It is certified that error appears in the above-identified patent and that said Letters Patent is hereby corrected as shown below:

Column 4, line 29, after "temperature," insert --by--.
    inserted.

Column 6, line 44, "3.14" should be -- 23.14 --.

Column 7, line 38, "5.77" should be -- 25.77 --.

Column 7, line 46, "120" should be -- $t_{120}$ --.

Column 11, line 5, "500" should be -- 1500 --.

Column 11, line 8, "500" should be -- 1500 --.

UNITED STATES PATENT AND TRADEMARK OFFICE
CERTIFICATE OF CORRECTION

PATENT NO. : 5,260,188
DATED : November 9, 1993
INVENTOR(S) : Prakash N. Rao

It is certified that error appears in the above-identified patent and that said Letters Patent is hereby corrected as shown below:

Column 13, line 29, the following should be inserted after "vein":
-- with 150 cc of cold (4°C) lactated ringer's solution. The --

Column 14, line 20, "result" should be -- results --.

Signed and Sealed this

Eleventh Day of July, 1995

BRUCE LEHMAN

Attest:

Attesting Officer

Commissioner of Patents and Trademarks